United States Patent [19]

Shaw

[11] Patent Number: 5,344,610
[45] Date of Patent: Sep. 6, 1994

[54] ASPIRATOR PROBE WITH LONG PIVOT ARM TO MINIMIZE TIP FLICK

[75] Inventor: James D. Shaw, Hilton, N.Y.
[73] Assignee: Eastman Kodak Company, Rochester, N.Y.
[21] Appl. No.: 12,681
[22] Filed: Feb. 3, 1993
[51] Int. Cl.5 .......................... B01L 3/02; G01N 35/06
[52] U.S. Cl. ...................................... 422/100; 422/63; 436/48
[58] Field of Search .................. 33/561, 706, 707; 422/63–68.1, 100; 436/48

[56] References Cited

U.S. PATENT DOCUMENTS

| | | | |
|---|---|---|---|
| 4,340,390 | 7/1982 | Collins et al. | 23/230 |
| 4,519,140 | 5/1985 | Schmitt | 33/125 C |
| 4,716,656 | 1/1988 | Maddock et al. | 33/561 X |
| 4,737,344 | 4/1988 | Koizumi et al. | 422/100 |
| 4,786,803 | 11/1988 | Majette et al. | 356/375 X |
| 4,793,067 | 12/1988 | Reiman et al. | 33/125 A |
| 4,824,641 | 4/1989 | Williams | 422/100 |
| 4,844,868 | 7/1989 | Rokugawa | 422/64 |
| 4,854,709 | 8/1989 | Mehnert et al. | 356/375 |
| 5,008,082 | 4/1991 | Shaw | 422/65 |
| 5,052,338 | 10/1991 | Maiorca et al. | 356/375 X |
| 5,114,854 | 5/1992 | Bertholdt | 435/240 |
| 5,115,573 | 5/1992 | Rieder et al. | 33/706 X |
| 5,142,792 | 9/1992 | Nelle | 33/706 X |

Primary Examiner—James C. Housel
Assistant Examiner—Milton I. Cano
Attorney, Agent, or Firm—Dana M. Schmidt

[57] ABSTRACT

An aspirator probe, such as is used with a disposable tip in a clinical analyzer. The probe is pivotable to allow for horizontal displacement error in seating the probe at a liquid-dispensing station. To reduce the amount of "tip flick" that occurs by pivoting the tip about the pivot point as the probe starts to withdraw from the liquid-dispensing station, the pivot point is located from the fulcrum at the liquid dispensing station, a distance that is at least five times the length of the disposable tip measured from the fulcrum.

4 Claims, 4 Drawing Sheets

ASPIRATOR PROBE WITH LONG PIVOT ARM TO MINIMIZE TIP FLICK

FIELD OF THE INVENTION

This invention relates to aspirating and dispense probes, and the stations at which they are vertically mounted to dispense liquid, especially in clinical analyzers.

BACKGROUND OF THE INVENTION

Clinical analyzers conventionally use an aspirator probe to aspirate sample into a disposable tip, and then dispense some of that sample onto a slide element that has dried reagents therein. Such a sequence is schematically illustrated in, e.g., U.S. Pat. No. 4,340,390, FIG. 2 thereof. It is also conventional to provide for some compliance in the horizontal mounting of the probe, to allow for slight displacement errors in the seating of the tip at, e.g., the sample-dispensing station. Such compliance is conventionally achieved using a vertically depending, pivotable spring a short distance above the seating surface of the tip, the spring allowing for the horizontal displacement.

Such a design has worked well in most instances. However, occasionally there is a problem due to the amount of horizontal displacement incurred at the sample dispensing station. Although structure is provided to accurately "seat" the tip for dispensing, notwithstanding such displacement, when the tip starts to withdraw, the displacement force, still present, acts to slightly pivot the tip above its vertical axis. I have discovered that if, as with some chemistries, the dispensed sample has not been completely absorbed, this pivoting can lead to what is called "tip flick". That is, the residual liquid above the surface of the slide is flicked off center, causing the slide to "read" as though the dispensing occurred off-center. Such off-center locations of the sample can interfere with accurate detection of the concentration of the analyte in question.

Accordingly, prior to this invention there has been a need to prevent "tip flick" by some mechanism.

RELATED APPLICATIONS

Commonly owned U.S. Ser. No. 954,632 now U.S. Pat. No. 5,273,717 filed on Sep. 30, 1992 by R. Marvin, entitled SELF-CALIBRATING ANALYZER ASPIRATOR, discloses but does not claim a mounting arm that pivots about a point far removed from the pivot fulcrum, compared to the length of the disposable tip. This feature of that application was derived from the instant invention.

SUMMARY OF THE INVENTION

I have constructed a probe structure that drastically reduces the amount of "tip flick" that can occur.

More specifically, there is provided an aspirator probe for aspirating and dispensing liquid, the probe comprising a support shaft and a tip-mounting surface connected to the shaft for a disposable tip having a seating surface and a dispensing orifice, the support shaft being disposed generally vertically and including pivotable compliant means for allowing for horizontal displacement of the tip at a liquid-dispensing station, the exterior surface of the tip adjacent to its seating surface acting as a fulcrum for inadvertent tip-pivoting at the sample dispense station, causing a horizontal displacement of the liquid-dispensing orifice of the tip. The probe is improved in that the compliant means is pivoted vertically along the support shaft at a point from the tip mounting surface that is at least about five times the length of the tip from the seating surface to the tip orifice, whereby the horizontal displacement of the orifice due to the inadvertent pivoting, is minimized.

Accordingly, it is an advantageous feature of the invention that, through the use of a much longer pivot arm, the amount of "tip flick" is drastically reduced.

Other advantageous features will become apparent upon reference to the following "Detailed Description" when read in light of the attached drawings.

DESCRIPTION OF THE PREFERRED EMBODIMENTS

The invention is described hereinafter with respect to certain preferred embodiments, wherein the aspirator is used in a clinical analyzer to aspirate and dispense biological liquid onto a slide element such as those available from Eastman Kodak Co. under the trademark "Ektachem" slides. In addition, the invention is applicable to any vertically operated aspirator probe, whether in an analyzer or not and regardless of what receives the dispensed liquid, if it is desired that the dispensing be done at a predetermined location on that which receives it.

Figure 1:
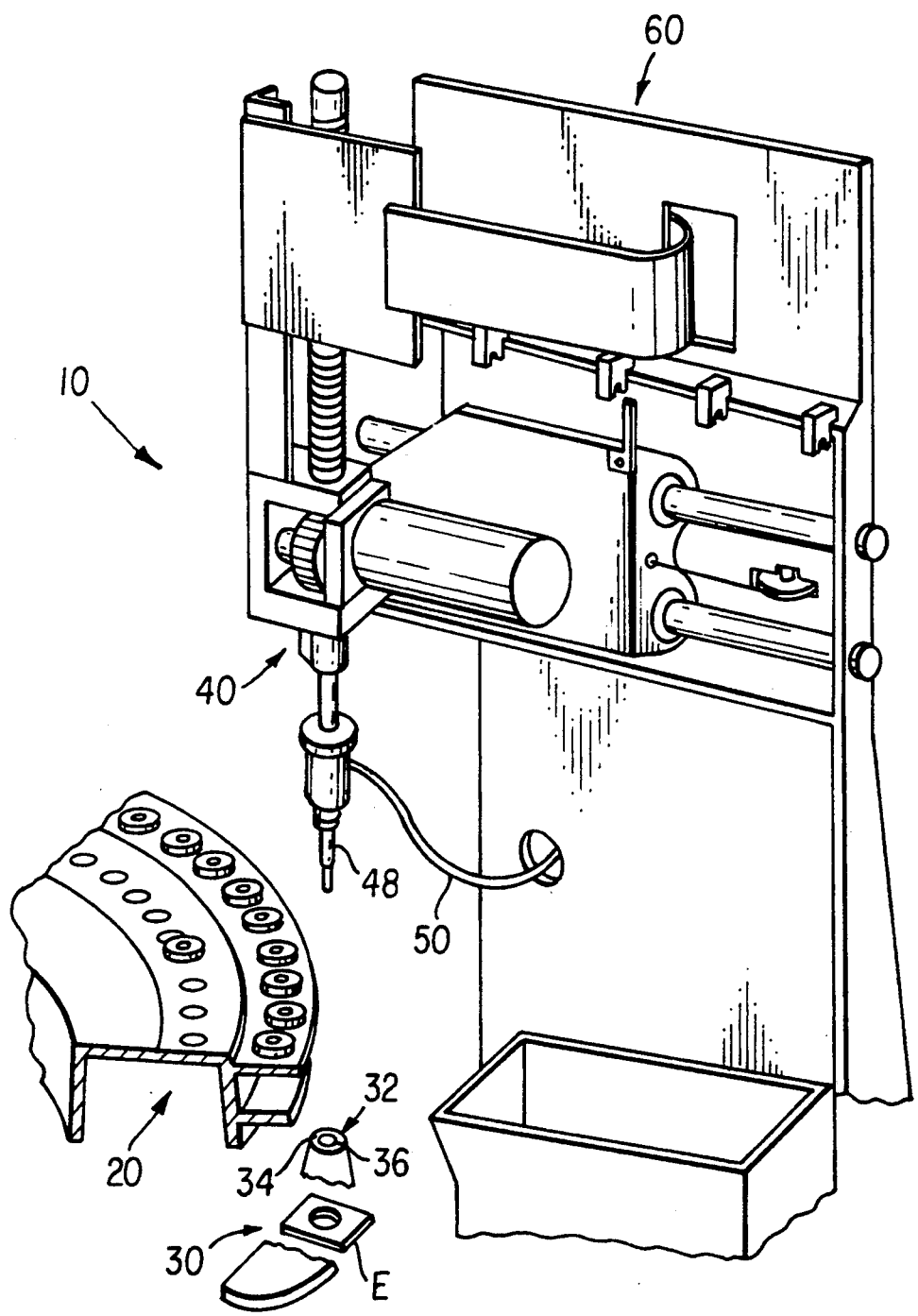
FIG. 1 is a fragmentary perspective view of a conventional aspirator probe, sample supply station, and dispensing station for dispensing liquid onto a slide element, in an analyzer.

FIG. 1 illustrates both the preferred environment of use (in a clinical analyzer), as well as the above-mentioned prior art. That is, an analyzer 10 conventionally includes a sample supply station 20; a liquid-dispensing station 30; an aspirator probe 40 having a disposable tip 48; means for controlling the vacuum and pressure in the probe, including an air hose 50; and a mechanism 60 for raising and lowering the probe and traversing it from sample supply station 20 to the dispensing station 30 where it is shown as being located. For further details of these stations and mechanism, reference is made to U.S. Pat. No. 4,340,390. It will be readily apparent that, to dispense liquid onto a slide E held at station 30, probe 40 is lowered until tip 48 enters into station 30 where it is seated. To that end, a tip locator cone 32 is provided at station 30, with a tip-seating surface 34 at the top and an entrance orifice 36.

Figure 2:
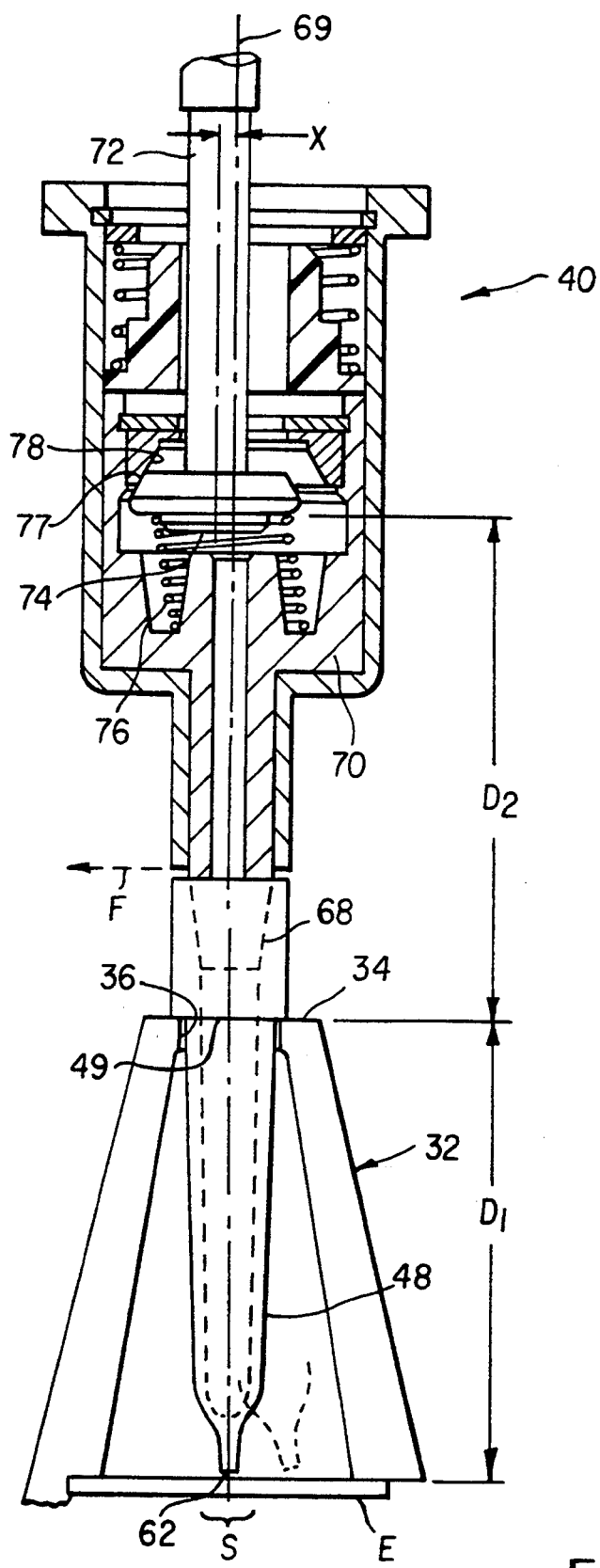
FIG. 2 is a fragmentary elevational view in section of a portion of the probe of FIG. 1, to illustrate further the problem.

Further details of the tip locator are shown in FIG. 2. That is, tip-seating surface 34 is located a fixed distance from slide element E such that end 62 of tip 48 is spaced a predetermined distance from slide element E. Orifice 36 acts to confine tip 48 in the horizontal plane, that is, precisely over the spot "S" on element E on which the liquid is to be dispensed.

Probe 40 conventionally mounts tip 48 at cone end 68. Probe 40 further includes a mechanism that provides both horizontal compliance and vertical compliance, to adjust for positional errors vis-a-vis locator 32. That is, probe 40 comprises an exterior housing 70 that loosely surrounds probe shaft 72 and which is biased away from end 74 of shaft 72 by a compression spring 76. End 74 in turn is cone-shaped at 77 to allow it to seat in a matching cone surface 78 that is part of housing 70, when spring 76 has expanded as much as it can.

As a result, a horizontal positional error X can occur for shaft 72, off the axis 69 of housing 70, when the probe seats in tip locator 32. This error does not immediately affect the dispensing, due to the constraint provided for by orifice 36. It is, however, a pending error, which makes itself apparent as soon as probe 40 starts to rise from locator 32 after dispensing. That is, tip 48 has its own seating surface 49 that mates with surface 34, as shown. When probe 40 starts to rise and surface 49 starts to release from surface 34, spring 76 starts to recenter shaft housing 70 onto shaft 72 to get rid of error "X". This in turn creates a pivot force F as shown, that causes tip 48 to pivot to the right (as shown in phantom) about its surface 49, with a pivot arm $D_1$ about the fulcrum provided by surface 34. The total distance pivoted is controlled by the length of the displacement arm shown as $D_2$, which in turn is measured between the fulcrum of surface 34 and the seat of spring 76 on end 74.

It turns out that distances $D_1$ and $D_2$ are approximately equal, that is, arm $D_2$ that induces the pivoting to account for error "X" is about equal to the length of tip 48 measured from surface 49.

The pivoting of the tip as shown in phantom causes what is known as "tip flick" in those instances in which the liquid already dispensed has not been completely absorbed by the test element.

Figure 3:
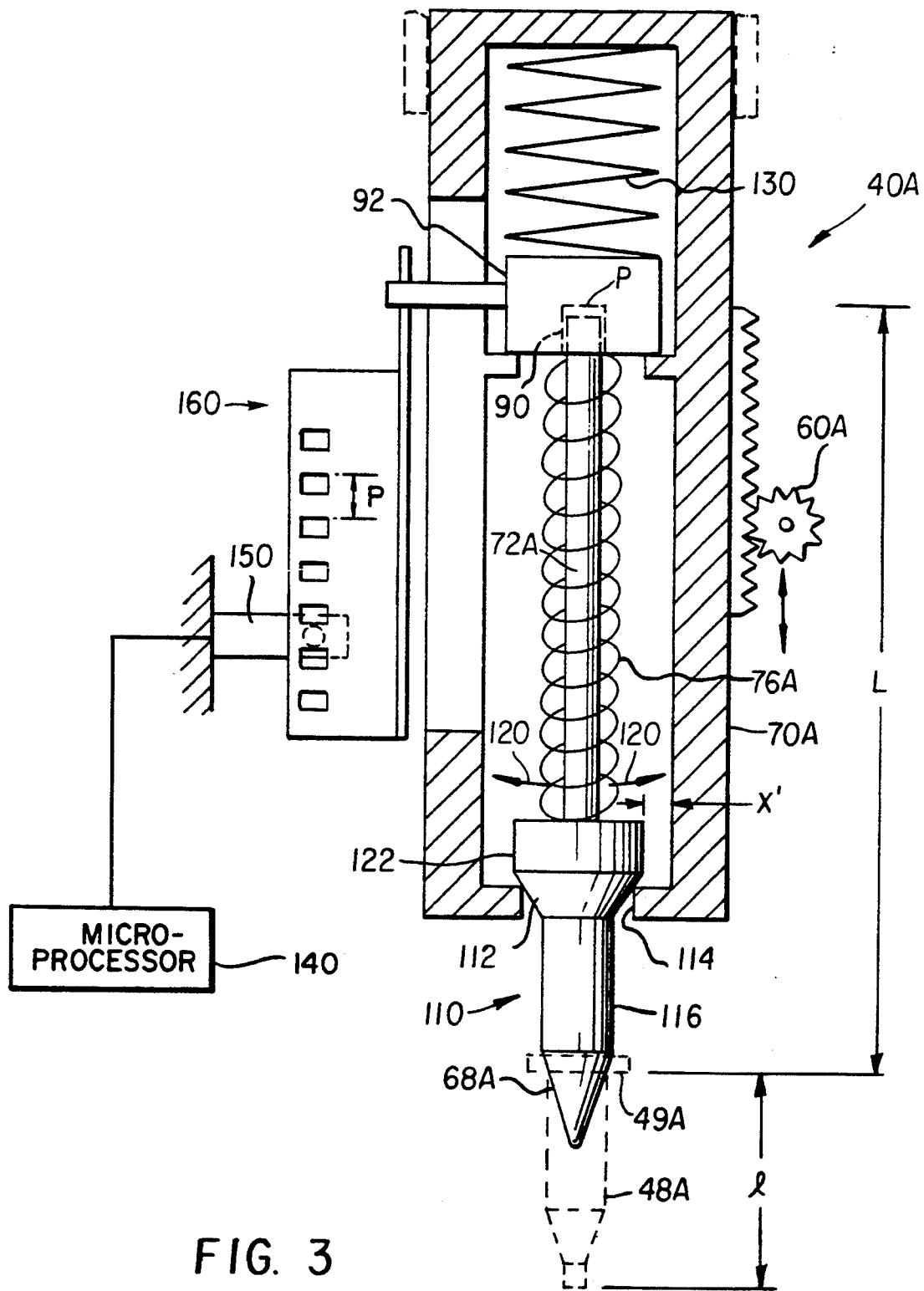
FIG. 3 is an elevational view similar to that of FIG. 2, but of the improvement of the invention.

In accordance with the invention, "tip flick" is minimized by drastically extending the length of arm $D_2$ so that it equals at least five times the length $D_1$, hereinafter "l" of tip 48 measured from its fulcrum surface. Referring now to FIG. 3, a construction is shown that replaces the probe of FIGS. 1 and 2, except that the same or similar mechanism (60A) is used to provide vertical and horizontal displacement of the probe, as needed. Parts similar to those previously described bear the same reference numeral, to which the distinguishing letter "A" is appended.

Thus, probe 40A mounts a disposable tip 48A on a cone surface 68A, with a housing 70A that loosely surrounds a shaft 72A generally as described above for the prior art probe. However, unlike the prior art, shaft 72A is seated in a depression 90 in a block 92 and the vertical compliance is due to a compression spring 76A surrounding most of shaft 72A. The intersection of block 92 by shaft 72A creates the pivot point for the entire probe down to and including tip 48A which is essentially a rigid arm. A cone 110 is mounted on the end of shaft 72A, with a conical surface 112 that mates with an opening 114 when spring 76A is fully extended. However, cone 110 has a cylindrical portion 116 that is considerably smaller than the opening 114, so that when cone 110 is pushed up against spring 76A by the tip locator (not shown) at the dispensing station, shaft 72A is free to pivot, arrows 120, about pivot point P in depression 90, until cone 110 strikes either opening 114 with cylindrical portion 116, or the inside of housing 70A with upper portion 122 connected to cone surface 112. The horizontal extent of the pivoting, arrows 120, introduces the pending displacement error X which may or may not be the same quantitative value as error "X" of the prior art. However, this error is controlled now by a pivot arm L, measured from fulcrum surface 49A of the tip, all the way back to pivot point P, which is at least 5 times the tip length "l" measured from that same fulcrum surface. (FIG. 3 has been fore-shortened for ease of drawing, so that L does not appear to be quite as much as $5 \times l$.)

Because shaft 72A, cone 110 and tip 48A comprise one rigid arm, any displacement error $X^1$ that does occur will of course misalign the axis of this rigid arm slightly off vertical. However, the small amount that this disturbs tip 48A from being vertical is of no consequence to the performance of the tip.

The other features of FIG. 3, including compression spring 130, microprocessor 140, sensor 150 and flag 160, are optional and not part of this invention, but are as described in the aforesaid commonly owned U.S. application Ser. No. 954,632. They are shown to illustrate that some sensing mechanism is preferred to allow the probe to sense when it and its tip 48A has descended the proper distance to pick up a tip, and preferably, only a tip. The sensing is a function of the movement of flag 160 past the sensor. Flag 160 ceases movement when cone 110 ceases movement (shaft 72A having bottomed out in depression 90 and housing 70A continues to advance against spring 130. Detection of the cessation, coupled with the number of flag windows that have gone past the sensor, informs the microprocessor how far the probe has descended.

Figure 4:
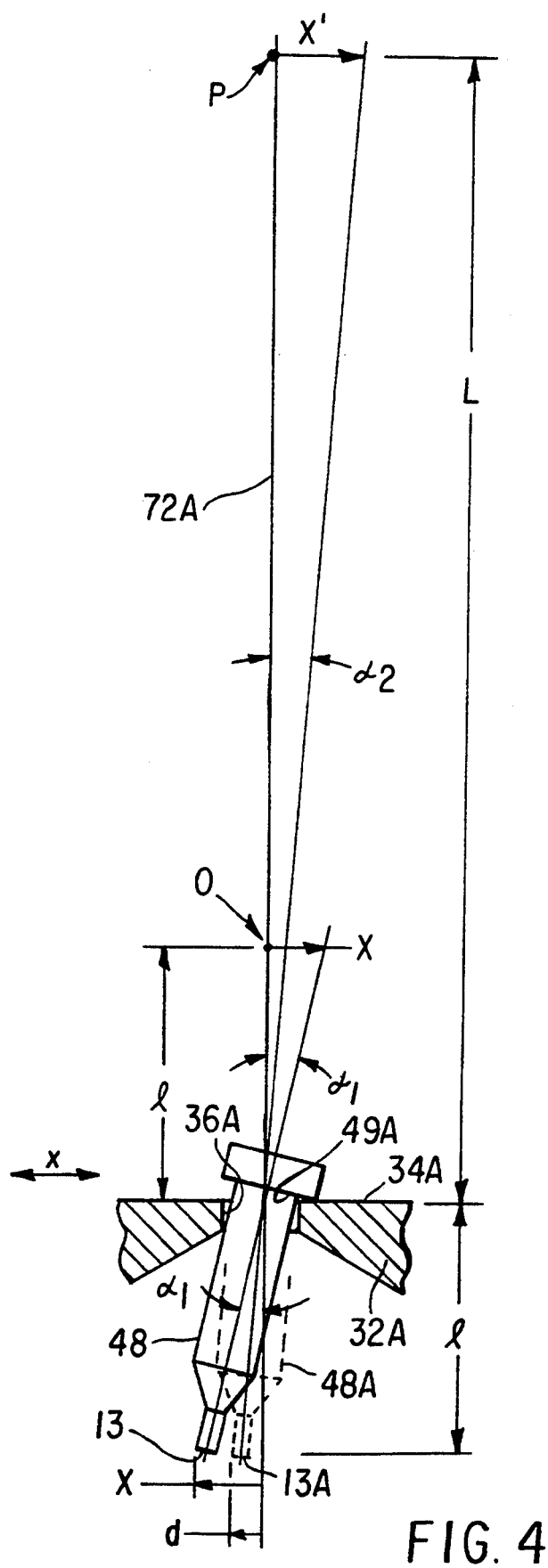
FIG. 4 is a diagrammatic analysis of the way in which the objective is achieved by the invention.

The manner in which error $X^1$ expresses itself, and the advantage of the instant invention, are further apparent from FIG. 4. The prior art construction is shown in solid lines for tip 48, by way of comparison. That is, displacement error X at pivot point 0, due to the construction shown in FIG. 2, becomes translated into displacement error X and a significant "tip flick", at tip aperture 13, given that arm l is about equal to overall length "l" of the tip measured from surface 49A.

In this invention, as with the prior art analyzer, tip 48A is seated in tip locator 32A and is constrained in the "x" direction by opening 36A of locator 32A. Tip surface 49A and locator surface 34A are the pivotal or fulcrum surfaces. Misalignment of the probe with locator 32A causes a displacement error $X^1$ of cone 110, FIG. 3, of up to about 0.8 mm.

As the probe of the invention lifts up from the tip locator, compliant spring 76A (FIG. 3) causes shaft 72A to pivot about point P to return the shaft to its vertical orientation and recover the pending error $X^1$. Tip 48A (shown in phantom, FIG. 4) pivots on surface 34A to allow this, and this creates tip movement d, the actual displacement error resulting from the "pending" error $X^1$. This movement "d" gives a reduced amount of "tip flick".

Since the displacement error of the invention that can occur is $X^1$, which can be equal to X of FIG. 2, the amount of pivoting, FIG. 4, that can occur once the tip unseats, provides a new pivot angle $\alpha_2$, smaller than 51 of the prior art, which can be defined as tan $\alpha_2 = X^1/L = X/5l$, where L is at least $5 = l$. But, the "tip flick" distance "d" with the invention, for tip 13A, also fits the equation:

$$\tan \alpha_2 \approx d/l.$$

Hence, $X/5l = d/l$, so that d clearly $\leq 1/5$ X, or no more than one-fifth the amount the tip tends to "flick" in the conventional design.

A highly preferred example is one in which $1 \leq 1/5.7$ X, because L=5.7.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In an aspirator probe for aspirating and dispensing liquid, said probe comprising a support shaft and a tip-mounting surface connected to said shaft for a disposable tip having a seating surface and a dispensing orifice, said support shaft being disposed generally vertically and including pivotable compliant means for allowing for horizontal displacement of said tip at a liquid-dispensing station, an exterior surface of said tip adjacent to its seating surface acting as a fulcrum for inadvertent tip-pivoting at the sample dispense station, causing a horizontal displacement of the liquid-dispensing orifice of the tip;

the improvement wherein said compliant means is pivoted vertically along said support shaft at a point from said tip mounting, surface that is at least about five times the length of said tip from said seating surface to said tip orifice, whereby the horizontal displacement of said orifice due to said inadvertent pivoting, is minimized.

2. A probe as defined in claim 1, wherein said compliant means comprises a compression spring surrounding at least a portion of said shaft.

3. A probe as defined in claim 2, wherein said liquid-dispensing station includes means for holding a slide test element, and a tip locator into which said tip is seated, said locator having a seating surface on which said tip seating surface acts as a fulcrum when said tip is first withdrawn from said seating surface of said locator.

4. A probe as defined in claim 1, wherein said liquid-dispensing station includes means for holding a slide test element, and a tip locator into which said tip is seated, said locator having a seating surface on which said tip seating surface acts as a fulcrum when said tip is first withdrawn from said seating surface of said locator.

* * * * *